(12) United States Patent
Gopi et al.

(10) Patent No.: US 10,953,068 B2
(45) Date of Patent: Mar. 23, 2021

(54) ANTI-INFLAMMATORY COMPOSITION FOR THE TREATMENT OF ACUTE JOINT INFLAMMATION AND A PROCESS FOR PREPARATION THEREOF

(71) Applicant: Aurea Biolabs Private Limited, Cochin (IN)

(72) Inventors: Sreeraj Gopi, Cochin (IN); Karthik Varma Ayiranazhi Covilakam, Cochin (IN); Robin George, Cochin (IN)

(73) Assignee: AUREA BIOLABS PRIVATE LIMITED, Kolenchery (IN)

( * ) Notice: Subject to any disclaimer, the term of this patent is extended or adjusted under 35 U.S.C. 154(b) by 0 days.

(21) Appl. No.: 16/312,562

(22) PCT Filed: Aug. 19, 2017

(86) PCT No.: PCT/IB2017/055025
§ 371 (c)(1),
(2) Date: Dec. 21, 2018

(87) PCT Pub. No.: WO2018/033891
PCT Pub. Date: Feb. 22, 2018

(65) Prior Publication Data
US 2019/0224267 A1 Jul. 25, 2019

(30) Foreign Application Priority Data
Aug. 19, 2016 (IN) .............................. 201641028193

(51) Int. Cl.
| | | |
|---|---|---|
| *A61K 36/9066* | (2006.01) | |
| *A61K 31/015* | (2006.01) | |
| *A61K 36/906* | (2006.01) | |
| *A61K 31/215* | (2006.01) | |
| *A61P 19/02* | (2006.01) | |
| *A61K 9/16* | (2006.01) | |
| *A61K 31/225* | (2006.01) | |
| *A61K 36/324* | (2006.01) | |
| *A61K 36/67* | (2006.01) | |

(52) U.S. Cl.
CPC ............ *A61K 36/9066* (2013.01); *A61K 9/16* (2013.01); *A61K 31/015* (2013.01); *A61K 31/215* (2013.01); *A61K 31/225* (2013.01); *A61K 36/324* (2013.01); *A61K 36/67* (2013.01); *A61K 36/906* (2013.01); *A61P 19/02* (2018.01); *A61K 2236/331* (2013.01); *A61K 2236/39* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 6,274,176 | B1 * | 8/2001 | Tomer ................... | A61K 36/28 424/725 |
| 9,101,599 | B2 * | 8/2015 | Gokaraju ................ | A61P 19/10 |
| 2008/0280996 | A1 * | 11/2008 | Pianowski .............. | A61P 17/06 514/763 |
| 2011/0159120 | A1 | 6/2011 | Gokaraju | |
| 2016/0113990 | A1 | 4/2016 | Cockburn | |

FOREIGN PATENT DOCUMENTS

WO 2015025263 A1 2/2015

OTHER PUBLICATIONS

Ridtitid (Planta Med (2009), vol. 75, PB33).*
Amalraj, Augustine, et al. "Acujoint™, a highly efficient formulation with natural bioactive compounds, exerts potent anti-arthritis effects in human osteoarthritis—A pilot randomized double blind clinical study compared to combination of glucosamine and chondroitin." Journal of Herbal Medicine vol. 17-18 (Sep. 1, 2019): 100276.
European Search Report for European Patent Application No. EP 17841193.0 dated Feb. 12, 2020.
IN-CHE-2015-05858A (Plant Lipids Pvt Ltd (IN) ) 1-905.05.2017 (May 5, 2017).
Jeena, Kottarapat, et al. "Antioxidant, Anti-Inflammatory and Antinociceptive Properties of Black Pepper Essential Oil (*Piper nigrum* Linn)." Journal of Essential Oil Bearing Plants 17.1 (2014): 1-12.
PCT International Search Report corresponding to PCT International Application No. PCT/IB2017/055025 dated Dec. 27, 2017.
Subramoniam, A., V. Madhavachandran, and A. Gangaprasad. "Medicinal Plants in the Treatment of Arthritis." Ann Phytomedicine 2 (2013): 3-36.
Vijayalaxmi, A., et al. "Anti-Arthritic and Anti Inflammatory Activity of Beta Caryophyllene against Freund's Complete Adjuvant Induced Arthritis in Wistar Rats." Journal of Bone Reports & Recommendations 1.29 (2015): 1-10.

* cited by examiner

*Primary Examiner* — Susan Hoffman
(74) *Attorney, Agent, or Firm* — Lempia Summerfield Katz LLC

(57) ABSTRACT

The present disclosure discloses an anti-inflammatory composition comprising turmeric alcohol extract, beta caryophyllene, 3-o-acetyl-11-keto-beta-boswellic acid, extract obtained from *Kaempferia galanga* and turmeric water extract. The present disclosure also describes a process of preparing the composition containing these extracts, which mainly involves extracting curcumin alcohol extract from turmeric, extracting gum resin from *Boswellia serrata*, AKBA is isolated from the extracted gum resin and complexed with phospholipid, beta-caryophyllene is isolated from *Piper nigrum* by steam distillation and subjected to fractionation for purification, flavonoids rich aqueous extract is extracted from *Kaempferia galanga* and turmeric water extract powder is obtained from *Curcuma longa*. The extracts are combined together to form a complete natural matrix, homogenized and subjected to spray drying to obtain a uniform mixture in a powdered form. The composition is useful as an anti-inflammatory agent in treatment of conditions such as acute joint pain and osteoarthritis.

5 Claims, 4 Drawing Sheets

| Sr.No | Ingredients | Composition (%) |
|---|---|---|
| 1 | Turmeric alcohol extract powder | 10-13 |
| 2 | Beta caryophyllene | 10-13 |
| 3 | 3-o-acetyl-11-keto-beta-boswellic acid | 13-15 |
| 4 | *Kaempferia galangal* extract | 27-30 |
| 5 | Turmeric water extract powder | 27-30 |

US 10,953,068 B2

ANTI-INFLAMMATORY COMPOSITION FOR THE TREATMENT OF ACUTE JOINT INFLAMMATION AND A PROCESS FOR PREPARATION THEREOF

CROSS-REFERENCE TO RELATED APPLICATION

The present patent document is a § 371 nationalization of PCT Application Serial No. PCT/IB2017/055025, filed Aug. 19, 2017, designating the United States, which is hereby incorporated by reference, and this patent document also claims the benefit of Indian Application No. 201641028193, filed Aug. 19, 2016, which is also hereby incorporated by reference.

TECHNICAL FIELD OF THE DISCLOSURE

The present disclosure discloses a composition comprising turmeric alcohol extract, beta caryophyllene, 3-o-acetyl-11-keto-beta-boswellic acid (AKBA), extract obtained from *Kaempferia galanga* and turmeric water extract. The present disclosure also describes a process of preparing the formulation containing the herbal extracts. The composition is useful as an anti-inflammatory agent in treatment of inflammatory conditions such as acute joint pain and osteoarthritis.

BACKGROUND

Joints are the structures that connect two or more bones in the body. They are found in many parts of the body such as the hips, the knees and the hands. Kinesthetic receptors are primarily stretch receptors, which are located in the muscles and joints. The kinesthetic receptors monitor the position and movements of muscles, bones, and joints.

The principal muscle receptor in kinesthesia is the muscle spindle, which includes both the primary and secondary endings of spindles. Primary endings are responsive to the size of a muscle length change and its speed thus detecting both position and movement of the muscles whereas the secondary endings are responsive only to the sense of position.

Inflammation is a protective response of the body to any injury, irritation, or surgery, which increases the blood flow to the local area, resulting in accumulation of fluid. Generally, the symptoms of inflammation include swelling, pain and redness of the skin.

Joints are also surrounded and cushioned by soft tissues. Accumulation of fluid in these soft tissues results in inflammation or swelling. The resulting joint pain and stiffness are also associated with inflammation. Upon triggering the inflammation, the immune system releases different chemicals such as cytokines or other inflammatory compounds that transmit pain signals to the brain. These chemicals include different Interleukins (IL) namely IL-1, IL-6, IL-15, IL-17, and IL-18, Tumor Necrosis Factor (TNF), Prostraglandins (PG) and peptides.

Osteoarthritis is the most common form of arthritis and is associated with degradation of articular cartilage, muscle weakness, synovitis, joint pain, inflammation and dysfunction. Generally, osteoarthritis affects 10%-15% of the world population and is a major cause of disability not only in elderly population but also in work force population and may be the fourth leading cause of disability by year 2020.

Generally, chondroitin and glucosamine combination is widely used in the treatment of osteoarthritis. Even though, the combination is effective in ameliorating the pain and improving the joint function, glucosamine is associated with mild gastrointestinal symptoms at high doses. Hence, phytonutrients may be helpful as alternative strategy for effective treatment of osteoarthritis. Hence, there is a need to analyze the potential effect of herbal formulation as a complementary treatment in addition to available routine therapies for improvement of symptoms of osteoarthritis.

The available treatment uses drugs, which are being developed and are intended to inhibit the activity of the different inflammatory chemicals. However, these drugs exhibit side effects such as breakdown in digestive mucus and prevention of normal healing processes. They also tend to affect cellular immune functions and secretions of various cytokines.

The U.S. Pat. No. 6,274,176 titled "Herbal compositions and their use as anti-inflammatory agents for alleviation of arthritis and gout" discloses an edible composition for use as an anti-inflammatory agent for alleviation of arthritis and gout in mammals, which comprises herbs such as *Tanacetum parthenium, Zingiber officinale* and *Curcuma longa*. This disclosure describes use of herbs as an anti-inflammatory agent for alleviation of arthritis and gout only and does not specify its use for other inflammatory conditions particularly acute joint pain.

The U.S. Pat. No. 9,101,599 titled "Synergistic anti-inflammatory compositions comprising *Boswellia serrata* extracts" discloses synergistic nutraceuticals or pharmaceutical or dietary supplement anti-inflammatory compositions comprising a combination of 3-O-acetyl-11-keto-β-boswellic acid (AKBA) and *Boswellia serrata* non-acidic resin extract (BNRE), which is used to prevent, control and treat inflammation. This disclosure relates to compositions combining only *Boswellia* extract, especially AKBA and BNRE for the prevention, control and treatment of inflammatory conditions. The disclosure discloses the use of *Boswellia* and not in combination for treatment of inflammation.

The US application number US20160113990 titled "Herbal formulation of an edible oral turmeric, its derivatives and other ingredients for the management of inflammation and chronic pain" discloses a formulation using turmeric, curcumin and *Boswellia serrata* for treatment of chronic pain and inflammation along with a fatty acid component namely alpha lipoic acid and other taste masking ingredients. This disclosure describes the use of edible formulation, which utilizes taste masking ingredients along with active herbal moieties.

There are many therapies available for the treatment of joint inflammation such as allopathic treatment, homeopathic treatment and herbal treatment. Allopathic treatment is a symptomatic treatment i.e., it treats the symptoms only but not the root cause. Herbal medicines are the oldest form of medicines known to humans. Herbal medicines have many advantages, which mainly include reduced side effects on the body, useful for the treatment of chronic pain, cost effective and easily available.

Presently, there are many herbal-containing compositions available for treatment of inflammation; however there is continually a need to provide alternative herbal compositions capable of reducing inflammation, which is particularly useful for the treatment of acute joint pain and osteoarthritis.

Thus, the object of the present invention is to provide a composition containing herbal medicines, which is useful for the treatment of various anti-inflammatory conditions mainly acute joint pain and osteoarthritis.

SUMMARY

The disclosure relates to a composition comprising turmeric alcohol extract, beta caryophyllene, 3-o-acetyl-11- keto-beta-boswellic acid (AKBA), extract obtained from *Kaempferia galanga* and turmeric water extract. The present disclosure also describes a process of preparing the formulation containing the herbal extracts. The composition is useful as an anti-inflammatory agent in treatment of conditions such as acute joint pain and osteoarthritis.

The herbal composition comprises turmeric alcohol extract powder at a concentration in the range of 10-13% w/w, beta-caryophyllene obtained from black pepper at the concentration in the range of 10%-13% w/w, AKBA at the concentration in the range of 13%-15% w/w, flavonoid extract obtained from *Kaempferia galanga* at the concentration in the range of 27%-30% w/w and turmeric water extract powder at the concentration in the range of 27%-30% w/w.

The disclosure further discloses a process for preparation of the composition. The disclosure involves the steps of extracting turmeric alcohol extract from turmeric. In the further step, gum resin from *Boswellia serrata* is extracted with ethanol solvent. Further, AKBA is isolated from the extracted gum resin and complexed with phospholipid to enhance the bioavailability of AKBA, which constitutes as a polar entity. In the next step, beta-caryophyllene is isolated from *Piper nigrum* by steam distillation and subjected to fractionation for purification and acts as non-polar entity. Flavonoids rich aqueous extract is extracted from *Kaempferia galanga*. The turmeric water extract is also obtained. Finally, the extracts are combined together to form a complete natural matrix, homogenized and subjected to spray drying to obtain a uniform mixture in a powdered form.

The composition in the form of capsule at a concentration of 250 mg is tested in patients with knee osteoarthritis. The parameters such as pain and functional disability are evaluated and results shows that the composition is effective in reducing the severity of pain, discomfort and physical disability in patients. The composition is also effective in improving the general condition and quality of life and improving the symptoms of patients.

The composition acts as anti-inflammatory agent. The composition is effective in reducing the pain and discomfort in patient with osteoarthritis.

DETAILED DESCRIPTION

The present disclosure discloses a composition comprising turmeric alcohol extract, beta caryophyllene from *Piper nigrum*, 3-o-acetyl-11-keto-beta-boswellic acid (AKBA) from *Boswellia serrata*, aqueous extract of turmeric powder, extract obtained from *Kaempferia galanga* in a fixed ratio based on complete natural matrix. The composition is useful as anti-inflammatory agent in treatment of conditions such as acute joint pain and osteoarthritis. The present disclosure also describes a process of preparing the composition.

Figure 1:
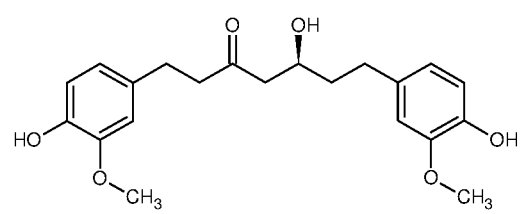
FIG. 1 illustrates the structure of curcumin, which is a phenolic constituent.

FIG. 1 illustrates the structure of curcumin, which is a phenolic constituent. Curcumin is isolated from *Curcuma longa*. The derivatives of curcumin include demethoxycurcumin and bisdemethoxycurcumin. Curcumin has the ability to suppress the effect of TNF-stimulation. Curcumin exhibits anti-inflammatory activity by up-regulation of Peroxisome proliferator-activated receptor (PPAR-γ), which results in the activation of PPAR-γ thus suppressing the release of inflammatory cytokines.

Figure 2:
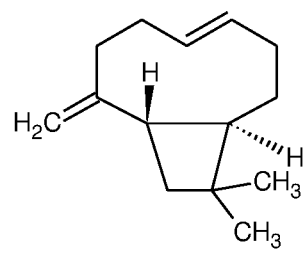
FIG. 2 illustrates the structure of beta-caryophyllene which is a sesquiterpene.

FIG. 2 illustrates the structure of beta-caryophyllene, which is a sesquiterpene. It is isolated from black pepper (*Piper nigrum*). It is found in large amounts in the essential oils of many different spices and food plants. The beta-caryophyllene binds to Tetrahydrocannabinol (THC) binding site of the peripheral hCB2 cannabinoid receptor thereby preventing the possible factor for inflammation.

Figures 3, 4:
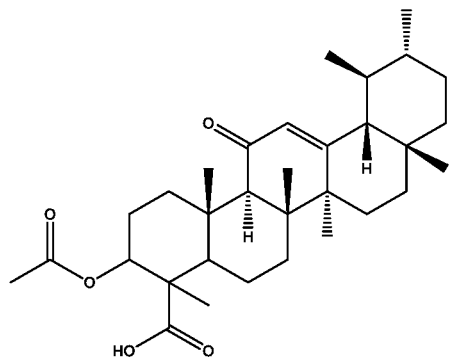
FIG. 3 illustrates the structure of 3-o-acetyl-11-keto-beta-boswellic acid.
FIG. 4 illustrates the anti-inflammatory composition of the present disclosure.

FIG. 3 illustrates the structure of 3-o-acetyl-11-keto-beta-boswellic acid (AKBA). AKBA isolated from *Boswellia serrata* provides support to the structural integrity, motility and comfort of joint cartilage. Boswellic acids helps in maintaining a healthy 5-lipoxygenase (5-LO) activity and also in moderating leukotriene biosynthesis, which plays a vital role in maintaining healthy Matrix Metalloproteinase (MMP) activity, which in turn supports the connective tissue structural composition. AKBA are inhibitors of 5-lipoxygenase (5-LO), nuclear factor kappa-B (NF-κB) pathway, leukocyte elastase, cathepsin G and microsomal prostaglandin E2 synthase (mPGES)-1. AKBA isolated from *Boswellia serrata*.

The preferred embodiment also comprises of extract obtained from *Kaempferia galanga*. The extract is used widely in anti-inflammatory formulations. *Kaempferia galanga* comprises the active principles namely 1'S'-1' acetoxychavicol acetate, 1'S-1'-hydroxychavicol acetate, trans-p-hydroxycinnamaldehyde. The active principle 1'S'-1' acetoxychavicol acetate exhibits anti-inflammatory, antimicrobial and anti-oxidative activities.

FIG. 4 illustrates the preferred composition of the formulation. The composition comprises curcumin alcohol extract powder at a concentration in the range of 10%-13% w/w, beta-caryophyllene obtained from black pepper (*Piper nigrum*) at the concentration in the range of 10%-13% w/w, AKBA at the concentration in the range of 13%-15% w/w, flavonoid extract obtained from *Kaempferia galanga* at the concentration in the range of 27%-30% w/w and turmeric water extract powder in the range of 27%-30% w/w.

Figure 5:
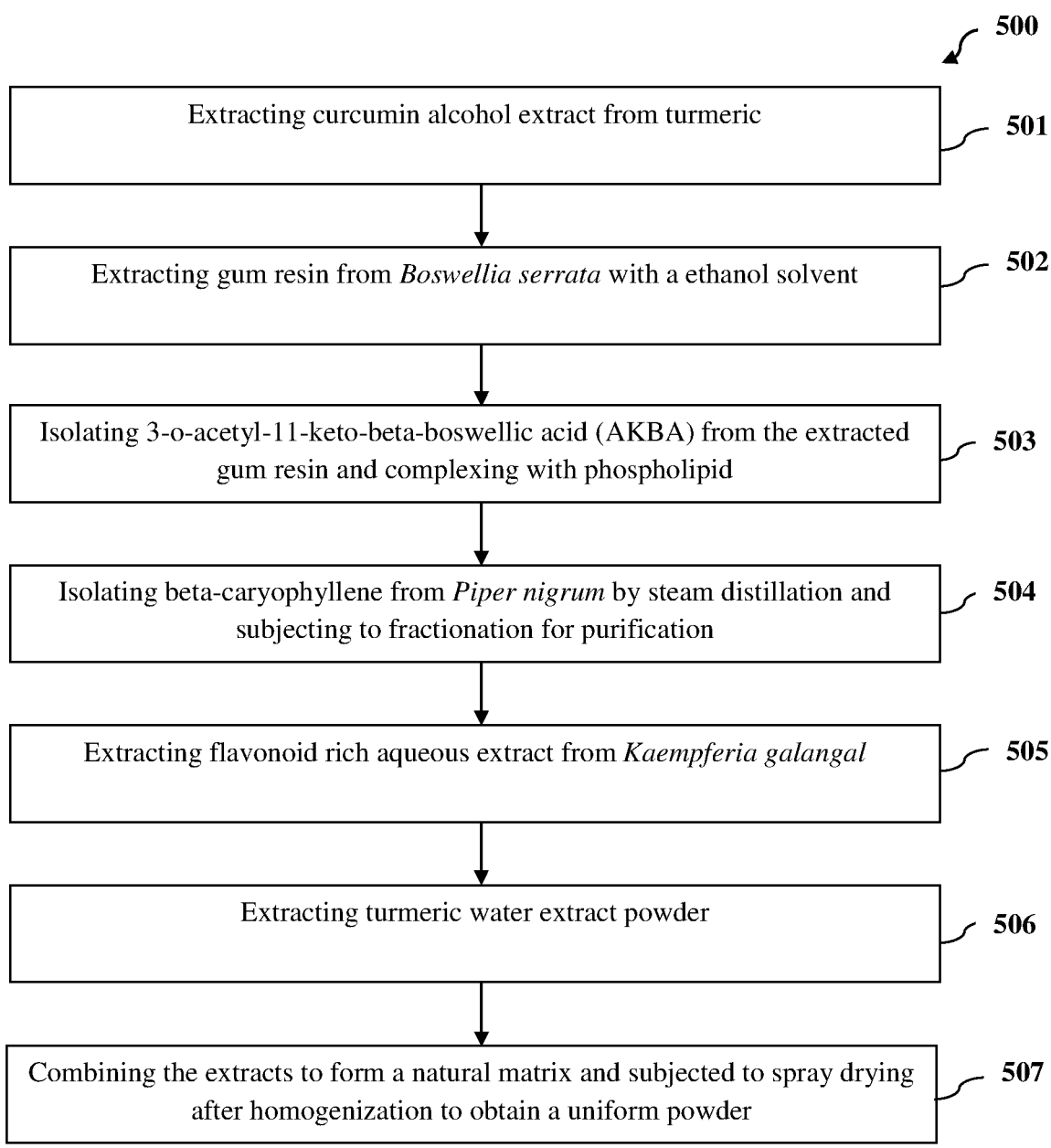
FIG. 5 illustrates a flow chart of a process of preparation of the anti-inflammatory composition.

FIG. 5 illustrates a flow chart of the process for preparation of the composition. The process (500) starts with a step (501) of extracting curcumin alcohol extract from turmeric. At step (502), gum resin from *Boswellia serrata* is extracted with a solvent. The gum resin is extracted using ethanol as a solvent. At step (503), AKBA is isolated from the extracted gum resin and complexed with phospholipid to enhance the bioavailability of AKBA, which is a polar entity. At step (504), beta-caryophyllene is isolated from *Piper nigrum* by steam distillation and subjected to fractionation for purification and acts as non-polar entity. At step (505), flavonoids rich aqueous extract is extracted from *Kaempferia galanga*. At step (506), turmeric water extract powder is extracted. At step (507), the extracts are combined together to form a complete natural matrix and homogenized and subjected to spray drying to obtain a uniform mixture in a powdered form.

In order that this disclosure to be more fully understood the following preparative and testing example is set forth.

The example is for the purpose of illustration only and is not to be construed as limiting the scope of the disclosure in any way.

Example 1: The Efficacy of the Composition for Treatment of Osteoarthritis

The composition of the disclosure is tested for treatment in patients with knee arthritis. The patients with knee osteoarthritis are subjected to treatment with the composition in the form of capsule at a concentration of 250 mg and are referred as treatment group and the patients with placebo are referred as reference group. The parameters such as pain and functional disability are evaluated. The composition is tested for efficacy on vital signs such as pain score, physical ability, WOMAC score i.e. the index of pain, stiffness and functional limitations, VAS score, Lequesne's functional index as an index of severity of osteoarthritis. The parameters are examined in different intervals of time such as on day 0, day 30, day 60 and day 90.

Figure 6:
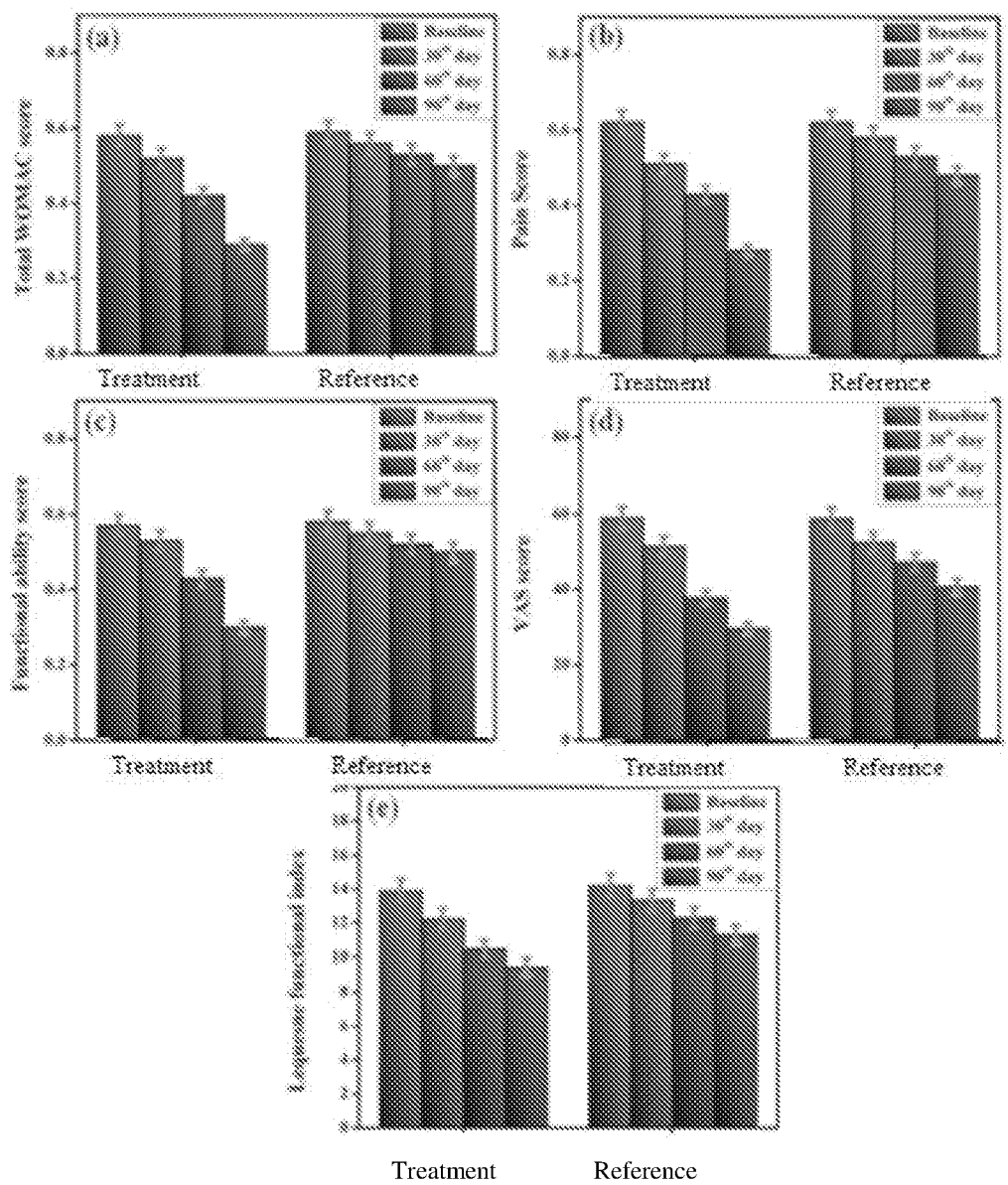
FIG. 6 illustrates difference in the parameters in the treatment and the reference group.

FIG. 6 illustrates difference in the parameters in the treatment and the reference group. The results show that the composition is effective in reducing the severity of pain, discomfort and physical disability in patients. The results further show that the patients exhibited significant change in total WOMAC score (P<0.001), pain score (P<0.001), functional ability score (P<0.001), VAS score (P<0.001) and Lequesne's functional index (P<0.001). It is also observed that that the mean percentage of the change in total WOMAC score are 49.70% in the treatment group in contrast to 15.54% in the reference group (FIG. 6a), pain score are 54.30% in the treatment group in contrast to 22.30% for reference group (FIG. 6b), functional ability score are 48.54% in the treatment group in contrast to 12.75% for reference group (FIG. 6c) and VAS score are 49.70% and 30.64% in the treatment group and the reference group respectively (FIG. 6d). Lequesne's function indexes are 32.06% and 20.53% in the treatment group and the reference group respectively (FIG. 6e).

Even though there is no significant differences of the parameters observed between the treatment group and the reference group when comparing the changes from baseline to day 30, there are significant differences observed between the two groups in total WOMAC score (P=0.006 and 0.0001), pain score (P=0.018 and 0.0001), functional ability score (P=0.016 and 0.0001), VAS score (P=0.009 and 0.0001) and Lequesne's functional index (P=0.031 and 0.045) at day 60 and day 90 respectively.

The composition is also effective in improving the general condition and quality of life and improving the symptoms of patients.

The herbal composition thus obtained acts as anti-inflammatory composition. The composition is effective in reducing the pain and discomfort in patient with osteoarthritis.

It is used in treatment and alleviation of various inflammatory conditions. The composition is majorly useful for the treatment of acute joint pain. The composition of the disclosure is effective for treatment of osteoarthritis with antioxidant, analgesic and anti-inflammatory effects.

We claim:

1. A composition for treatment of osteoarthritis, the composition comprising:
   a. turmeric alcohol extract powder at a concentration in the range of 10%-13% w/w;
   b. beta-caryophyllene obtained from *Piper nigrum* at the concentration in the range of 10%-13% w/w;
   c. 3-o-acetyl-11-keto-beta-boswellic acid (AKBA) from the extracted gum resin and complexed with phospholipid and used at the concentration in the range of 13%-15% w/w;
   d. *Kaempferia galanga* flavonoid rich aqueous extract at the concentration in the range of 27%-30% w/w; and
   e. turmeric water extract powder at the concentration in the range of 27%-30% w/w,
      wherein the extracts form a complete natural matrix and homogenization and spray drying forms a uniform mixture in a powdered form of the composition.

2. The composition as claimed in claim 1, wherein beta-caryophyllene is extracted from *Piper nigrum*.

3. The composition as claimed in claim 1, wherein AKBA is isolated from *Boswellia serrata* and provides support to the structural integrity, motility and comfort of joint cartilage.

4. The composition as claimed in claim 1, wherein the composition is effective in reducing the severity of pain, discomfort and physical disability in patients with osteoarthritis.

5. The composition as claimed in claim 1, wherein *Kaempferia galanga* comprises active principles namely 1'S'-1' acetoxychavicol acetate, 1'S-1'-hydroxychavicol acetate, trans-p-hydroxycinnamaldehyde.

\* \* \* \* \*